United States Patent [19]

Oumi et al.

[11] Patent Number: 4,597,381
[45] Date of Patent: Jul. 1, 1986

[54] APPARATUS FOR MONITORING AN ARTIFICIAL INTERNAL ORGAN

[75] Inventors: Takeharu Oumi, Toyota; Hideo Nakazawa, Tokyo, both of Japan

[73] Assignee: Aisin Seiki Kabushiki Kaisha, Aichi, Japan

[21] Appl. No.: 671,355

[22] Filed: Nov. 14, 1984

[30] Foreign Application Priority Data

Nov. 14, 1983 [JP] Japan .................. 58-213749

[51] Int. Cl.$^4$ .................................. A61B 1/04
[52] U.S. Cl. ........................ 128/6; 128/1 D; 358/98; 623/3
[58] Field of Search ............ 128/4, 6, 1 D, DIG. 3; 3/1.7; 358/98

[56] References Cited

U.S. PATENT DOCUMENTS

Re. 31,289  6/1983  Moore et al. .................. 128/6
4,016,871   4/1977  Schiff ......................... 3/1.7 X Primary Examiner—William H. Grieb
Attorney, Agent, or Firm—Sughrue, Mion, Zinn, Macpeak & Seas

[57] ABSTRACT

The apparatus is intended to monitor operation of an artificial internal organ, such as an auxiliary heart, which is to be attached to the patient's body on the outer side. An optical fiber for image pick-up and another optical fiber for illumination are mounted to the artificial internal organ, and a video camera, light source for illumination, control switches, monitor television unit, etc. are disposed in a position remote from the artificial internal organ. For the purpose of enlarging the monitoring range and providing illumination of high efficiency, a mirror is mounted in the artificial internal organ. An optical axis of the optical fiber for image pick-up is arranged to be opposite or perpendicular to that of the optical fiber for illumination.

7 Claims, 14 Drawing Figures

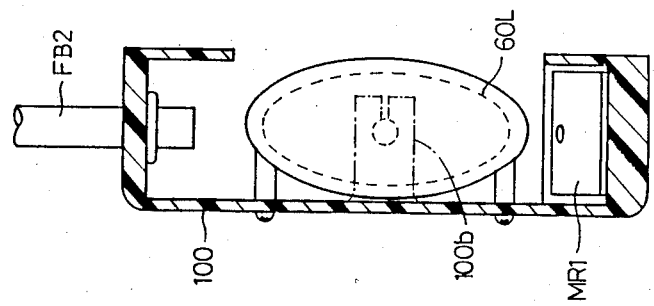
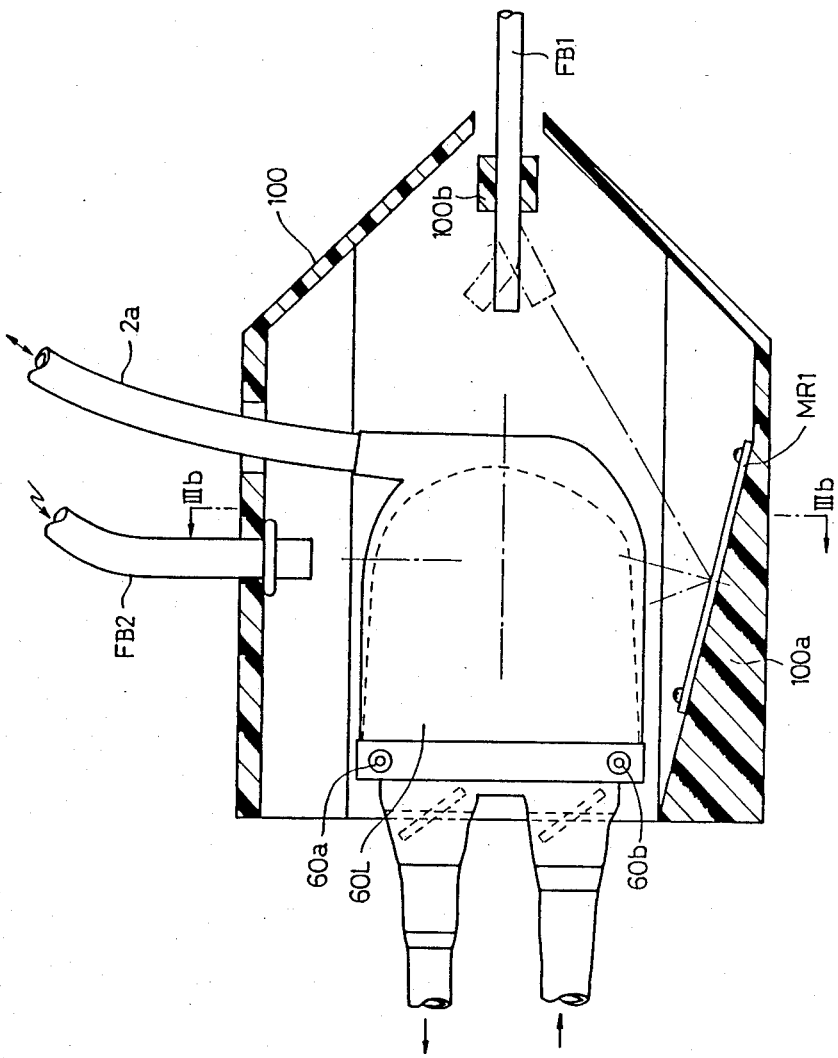

APPARATUS FOR MONITORING AN ARTIFICIAL INTERNAL ORGAN

BACKGROUND OF THE INVENTION

The present invention relates to an apparatus for monitoring the operating state of an artificial internal organ having movable portions such as an artificial heart.

Because of the absence of a practical long term artificial heart and difficulties in reducing the size of the entire system including a driving apparatus, etc., an artificial heart is not usually of, the type which is buried in the human body (i.e., perfect artificial heart) but rather is of the type that is attached onto the human body (i.e., auxiliary heart). An auxiliary heart is temporarily used for the purpose of compensating for the weakened physical strength of a patient during and after a surgical operation.

When using an artificial heart of this type, it is necessary to monitor the operating state thereof at all times. Stated differently, if any abnormally should be caused in a driving apparatus, artificial heart or the patient himself, it is impossible to anticipate what sort of failure will occur in the artificial heart correspondingly, and it can not be determined what action is to be taken in such an emergency case, until the doctor has checked the inside of the artificial heart.

Many artificial hearts are transparent and, if they remain as they are, the operating state of such artificial hearts can be directly observed from the outside. However, excepting the case of an animal experiment, when an auxiliary heart is actually attached to the human body, the artificial heart must be covered with cloth or bandages to thereby prevent, for example, bacterial infection through the parts where tubes of the artificial heart are led out of the body. For this reason it is impossible to observe the actual operating state of the artificial heart after it has been attached to the human body.

SUMMARY OF THE INVENTION

It is an object of the present invention to provide an apparatus for monitoring an artificial internal organ, which enables the monitoring of the actual operating state of the artificial internal organ, even if it has been covered with cloth or so after attachment onto the human body.

Use of optical fibers makes it possible to directly transmit local image information to a remote location in the form of a beam of light and the use of a video camera or the like makes it possible to convert the light transmitted over optical fibers to a television signal, etc. In the present invention, therefore, an optical fiber is disposed with one fore end thereof being directed to the movable portion of an artificial heart, i.e., the portion that is to be monitored, an illumination lamp is provided to illuminate the movable portion of the artifical heart, photo/electric conversion means such as a video camera is connected to the other end of the optical fiber, and information contained in an output signal from said means is visually displayed on a monitor television unit or the like.

In an endoscope equipped with an optical fiber, video camera, etc., for example, an illumination unit is housed in the optical fiber itself. However, since the movable portion of an artificial heart, for example, is filled with blood, it is difficult for an endoscope or the like to pick up an image of the entire portion to be monitored with satisfactory resolution. In a preferred embodiment of the present invention, therefore, at least one illumination lamp is provided in a position independent of the optical fiber for image pick-up and, more preferably, a beam of light emitted from the illumination is introduced to an artificial internal organ through another optical fiber. Further, in a preferred embodiment of the present invention, at least one reflection mirror is disposed in a position locating on an optical axis of the image pick-up optical fiber so as to enlarge the monitoring area.

Further, since an artificial internal organ is generally operated by a driving apparatus of relatively large size, such a driving apparatus must be always located near the artificial internal organ when it is monitored. In a preferred embodiment of the present invention, therefore, a monitor television unit, a control switch for monitoring device, etc. are provided on a driving apparatus for artificial internal organ. This makes it possible to change the setting of the driving parameters while monitoring the actual operating state of the artificial internal organ by the monitor television unit.

BRIEF DESCRIPTION OF THE DRAWINGS

FIG. 3a is a top plan view showing the artificial heart equipped with a monitoring device;

FIG. 3b is a sectional view taken on the line IIIb—IIIb in FIG. 3a.

DESCRIPTION OF PREFERRED EMBODIMENTS

In the following, preferred embodiments of the present invention will be described with reference to the drawings.

Figure 1:
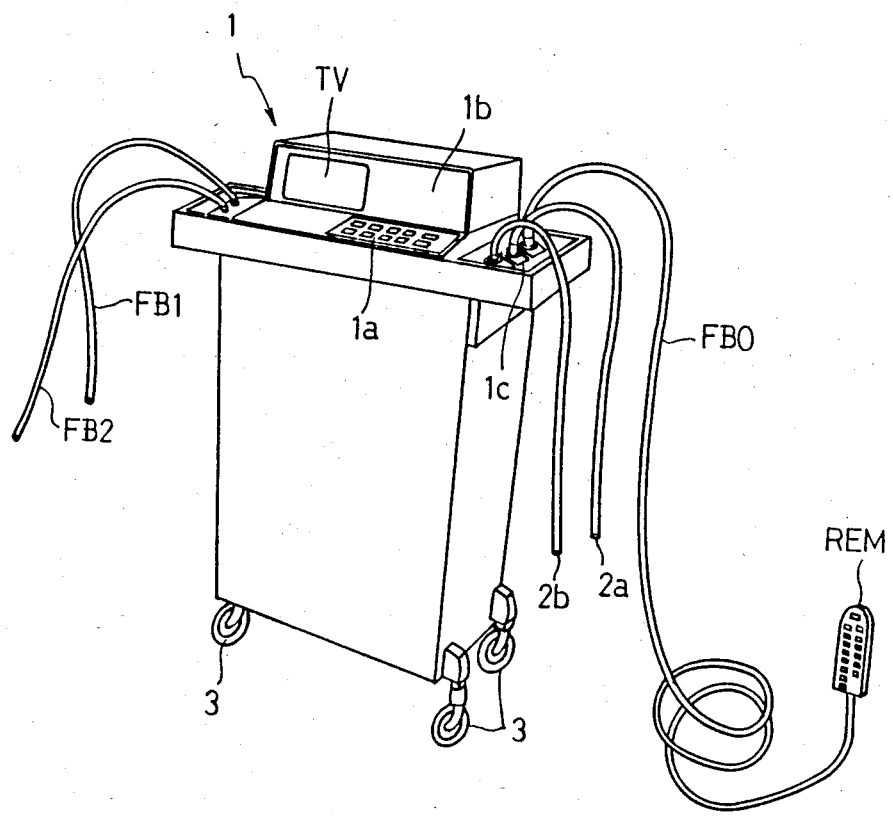
FIG. 1 is a perspective view of an apparatus for driving an artificial heart of the type embodying the present invention.

FIG. 1 illustrates external appearance of an artificial heart driving apparatus 1 (which is capable of driving also a balloon pump). Referring to FIG. 1, designated at 1a is a control section, at 1b is a display section and at 1c is a connecting section. Tubes 2a, 2b and an optical fiber cable FBO for remote control are connected to the connecting section 1c on the right side as viewed from front of the apparatus, and a remote control board REM is connected to the leading end of the optical fiber FBO.

Artificial hearts 60L and 60R (see FIG. 4) are connected to the tubes 2a and 2b, respectively. An optical fiber cable FB1 for image pick-up and an optical fiber cable FE2 for illumination are connected to the connection section on the right side as viewed from front of the apparatus.

As described later, a video camera CAM is connected to the optical fiber cable FB1 and an illumination lamp LMP is connected to the FB2. The video camera CAM and the lamp LMP are equipped for monitoring the actual operating state of the artificial hearts 60L, 60R. The display section 1b includes a monitor television unit TV for displaying an output from the video camera CAM. Designated at 3 is a caster.

Figure 2A:
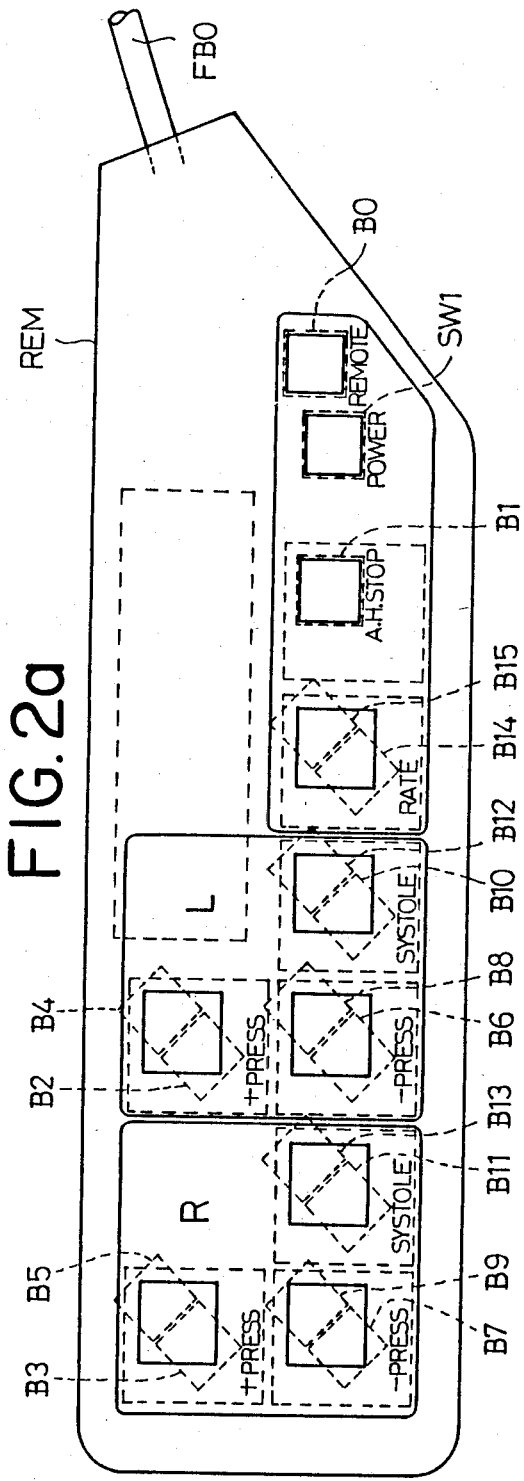
FIGS. 2a and 2b are a top plan view and front view of a remote control board REM, respectively.
Figure 2B:
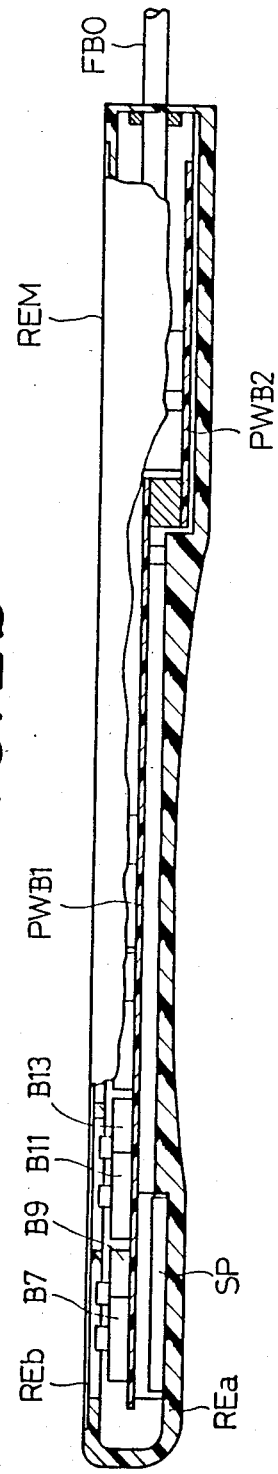

FIGS. 2a and 2b illustrate the mechanical construction of the remote control board REM. Description will now be made with reference to FIGS. 2a and 2b. A case REa of the control board is formed of synthetic resin. Squared openings are formed in an upper surface of the panel at those parts corresponding to switches, so that the switches may be operated, and those parts are covered with a thin resin sheet REb. Printed circuit boards PWB1 and PWB2 are integrally connected to each other. On the printed circuit boards PWB1 and PWB2 there are arranged seventeen switches SW1 and B0 to B15, a battery, a speaker SP, an optoelectrical converter, an electrooptical converter, etc.

FIGS. 3a and 3b illustrate an artificial heart 60L and a part of a unit for monitoring the operating state thereof. Description will now be made with reference to FIGS. 3a and 3b. The artificial heart 60L is screwed to a monitor case 100 at portions 60a, 60b.

In this embodiment, the optical fiber FB1 for image pick-up and the optical fiber FB2 for illumination are orthogonally disposed in a plane perpendicular to the depthwise direction of the artificial heart 60L so that they face the movable portion of the artificial heart 60L. Also, a reflection mirror MR1 is disposed in a position locating on the extended optical axes of both the optical fibers FB1 and FB2. It is to be noted that the optical fiber FB1 is further endowed with a function of illumination as with a conventional endscope, and that a fore end of the optical fiber FB1 is tiltable and can be remotely controlled.

Figure 4:
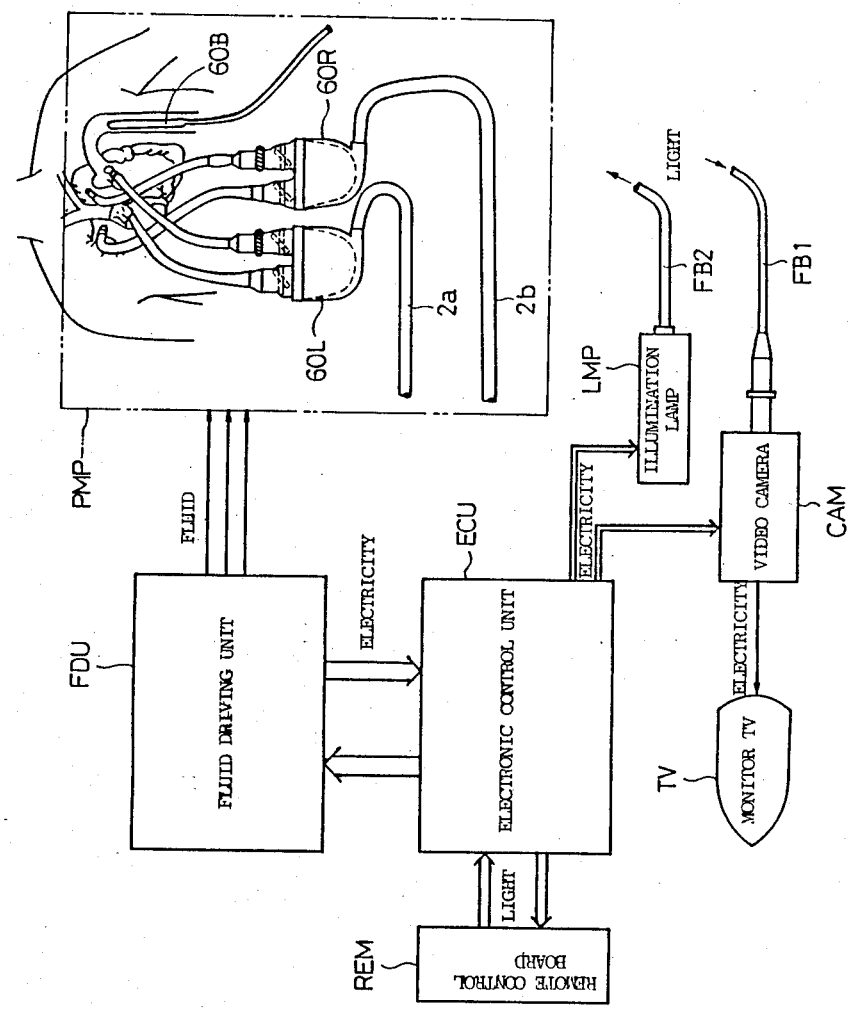
FIG. 4 is a block diagram showing the system configuration of the apparatus shown in FIG. 1.

FIG. 4 illustrates the system configuration of the apparatus shown in FIG. 1. Referring now to FIG. 4, designated at 60L and 60R are artificial hearts, and at 60B is a balloon pump in the main artery. A fluid driving unit FDU is provided with three fluid driving output terminals. But, since in practice the artificial hearts 60L, 60R and the balloon pump 60B are not used simultaneously, it is arranged that only two out of those three output terminals are operable simultaneously. Connected to an electronic control unit ECU for controlling the fluid driving unit FDU are the remote control board REM, the illumination lamp LMP and the video camera CAM. A signal output terminal of the video camera is connected to the monitor television unit TV. The remote control board REM and the electronic control unit ECU are interconnected through the optical fiber cable FBO, as previously noted.

Figure 5:
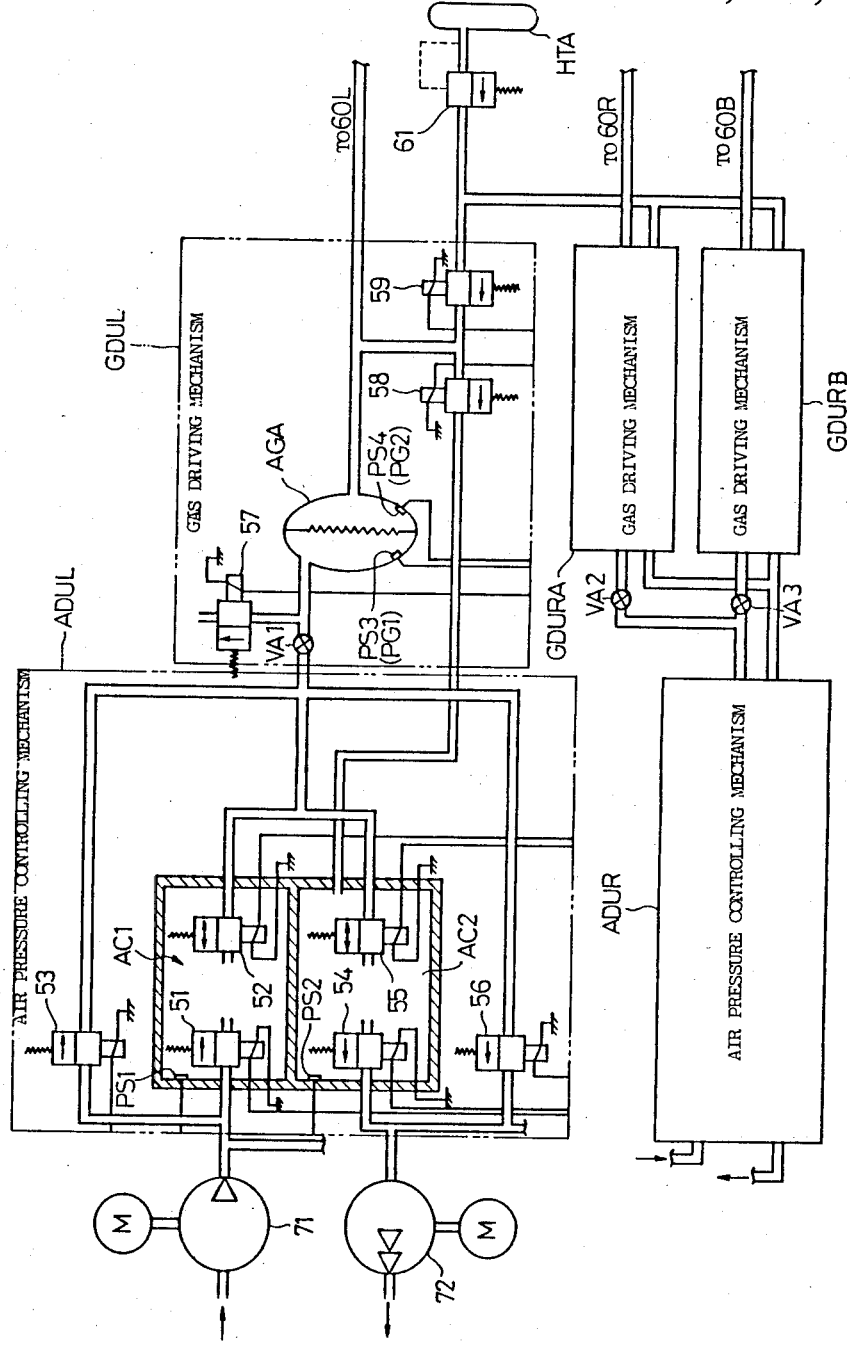
FIG. 5 is a block diagram showing the construction of a fluid driving unit shown in FIG. 4.

FIG. 5 illustrates the configuration of the fluid driving unit FDU in FIG. 4. First in brief, this unit FDU includes a compressor 71, a vacuum pump 72, air pressure controlling mechanisms ADUL and ADUR, gas driving mechanisms GDUL, GDRA and GDURB, a helium gas tank HTA, and a pressure reducing valve 61. An input terminal of the gas driving mechanism GDUL is connected to an output terminal of the air pressure controlling mechanism ADUL, while input terminals of the gas driving mechanisms GDURA and GDURB are commonly connected to an output terminal of the air pressure controlling mechanism ADUR. Output terminals of the gas driving mechanisms GDUL, GDURA and GDURB are connected to the artificial hearts 60L, 60R and the balloon pump 60B, respectively.

The air pressure controlling mechanism ADUL will now be described. This mechanism includes six solenoid valves 51, 52, 53, 54, 55 and 56. The solenoid valves 51, 52 and 53 are used for producing a positive pressure, while the solenoid valves 54, 55 and 56 are used for producing a negative pressure. The solenoid valves 51 and 52 are provided within an accumulator AC1, while the solenoid valves 54 and 55 are provided within an accumulator AC2. Input terminals of the solenoid valves 51 and 53 are connected to an output terminal of the compressor 71, input terminals (on the downstream side with respect to the running direction of a fluid) of the solenoid valves 54 and 56 are connected a negative pressure output terminal of the vacuum pump 72, and output terminals of the solenoid valves 52, 53, 55 and 56 are connected to the output terminal of the air pressure controlling mechanism ADUL. PS1 and PS2 designate pressure sensors for detecting pressures in the accumulators AC1 and AC2, respectively. The air pressure controlling mechanism ADUR has the same construction as the ADUL.

Next, the gas driving mechanism GDUL will be described. This mechanism includes solenoid valves 57, 58 and 59, a fluid isolator AGA, etc. The output terminal of the air pressure controlling mechanism ADUL is connected to the primary side (air side) of the fluid isolator AGA through a mechanical valve VA1. The solenoid valve 57 has an input terminal connected to the primary side of the fluid isolator AGA and an output terminal open to the atmosphere. The solenoid valve 59 has an input terminal connected to an output terminal of the pressure reducing valve 61 and an output terminal connected to the secondary side of the fluid isolator AGA. The solenoid valve 58 has an input terminal connected to the secondary side of the fluid isolator AGA and an output terminal connected to the inside of the accumulator AC2. The primary and secondary side of the fluid isolator AGA are provided with pressure sensors PS3 and PS4, respectively. The remaining gas driving mechanisms GDURA and GDURB have the same construction as the GDUL.

Figure 6:
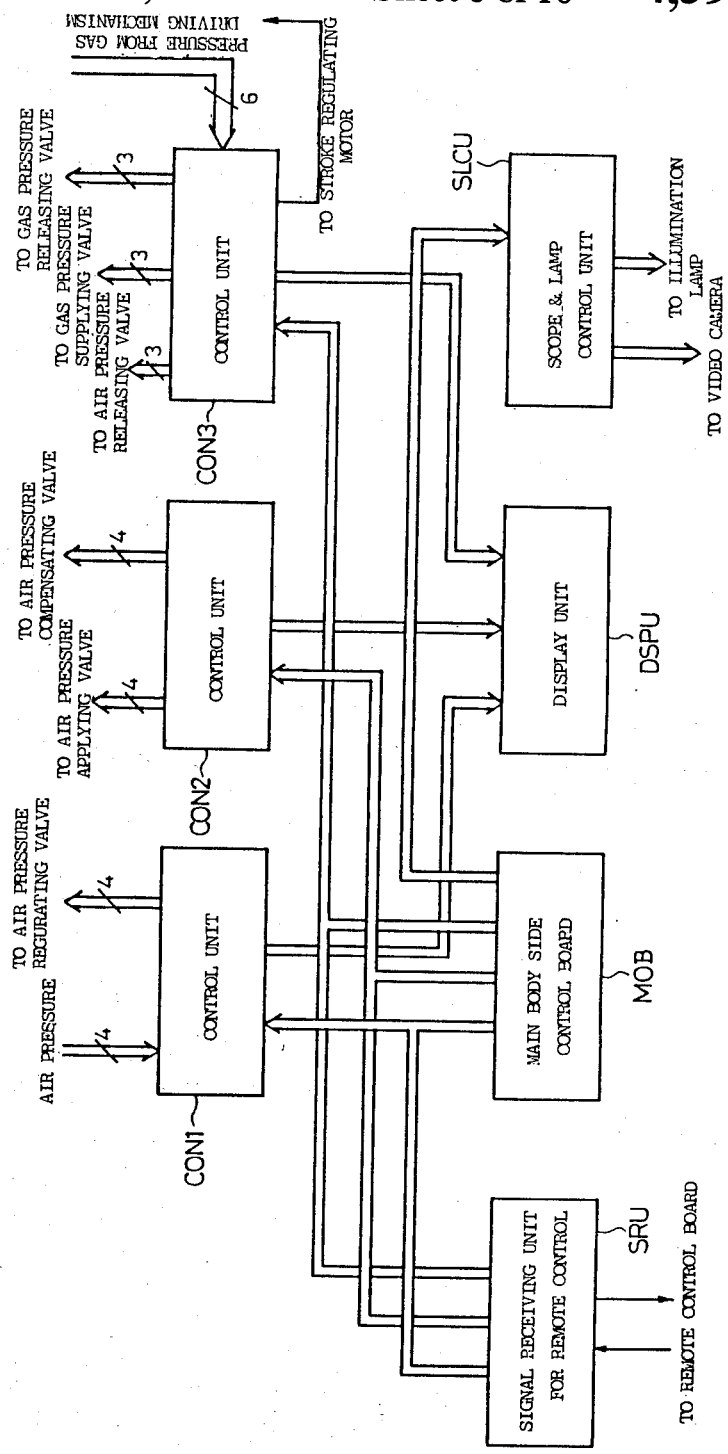
FIG. 6 is a block diagram showing the construction of an electronic control unit shown in FIG. 4.

FIG. 6 illustrates the configuration of the electronic control unit ECU shown in FIG. 4. Referring now to FIG. 6, the electronic control unit ECU is composed of control units CON1, CON2 and CON3, a signal receiving unit SRU for remote control, a main body side control board MOB, a display unit DSPU and a scope and lamp control unit SLCU.

The control unit CON1 monitors output signals from the pressure sensors PS1 and PS2 in the air pressure controlling mechanisms ADUL and ADUR, and then controllably open and close the solenoid valves 51 and 52 so that pressure in the accumulators AC1 and AC2 become equal to the preset values.

The control unit CON2 controllably opens and closes the solenoid valves 52, 53, 55 and 56 of the air pressure controlling mechanisms ADUL and ADUR at the given timing in accordance with the preset heartbeat period, respective systolic durations (or duty ratios) for right and left artificial hearts, etc.

The control unit CON3 controls the solenoid valves 57, 58 and 59 of the gas driving mechanisms GDUL, GDURA and GDURB. It is to be noted that the GDURA and GDURB will never be controlled simultaneously. The GDUL and GDURA are controlled by monitoring output signals (PG1, PG2) from the pressure sensors PS3 and PS4, while the GDURB is controlled without monitoring the output signal from the pressure sensor PS3. During control of the GDURB, the motor M1 is controlled.

The display unit DSPU comprises a number of 7-segment indicators and is connected to the control units CON1, CON2 and CON3. The main body side control board MOB is connected to the control units CON1, CON2 and CON3 as well as the scope and lamp control unit SLCU. Output lines of the signal receiving unit SRU for remote control are connected similarly to the corresponding signal lines of the main body side control board MOB, respectively.

Figure 7:
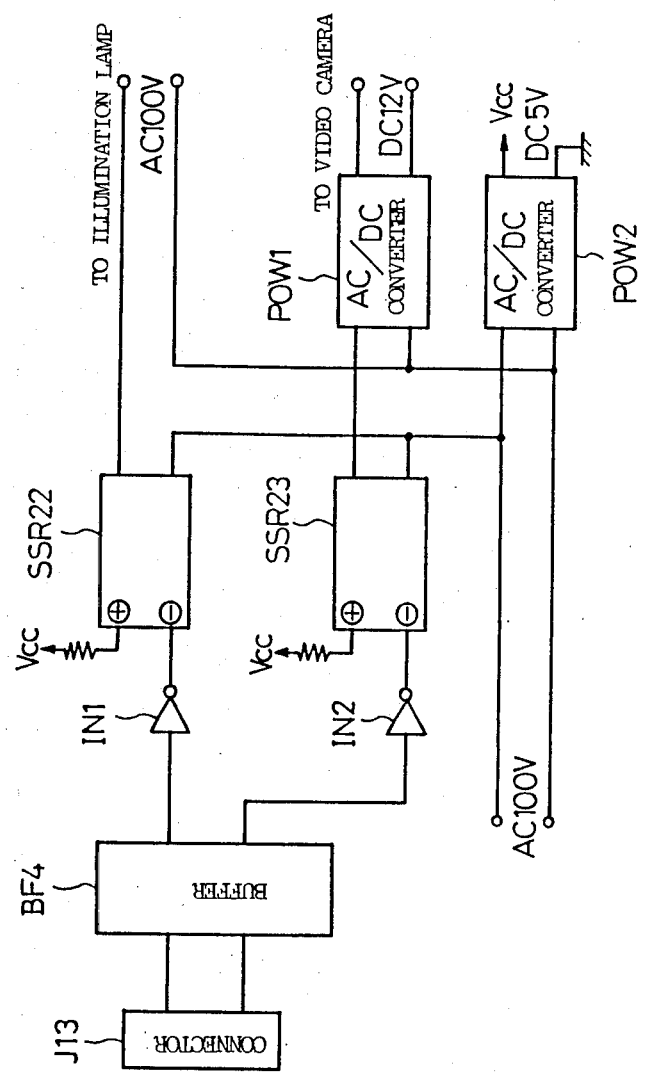
FIG. 7 is a block diagram showing the construction of a scope and lamp control unit shown in FIG. 6.

FIG. 7 illustrates the configuration of the scope and lamp control unit SLCU in FIG. 6. This unit SCLU is composed of a buffer B4, solid state relays SSR22 and SSR23, inverters IN1 and IN2, AC/DC converters (i.e., DC power supply units) POW1, POW2, etc., output terminals of the SSR22 and the POW1 being connected to the illumination lamp LMP and the video camera CAM, respectively. The POW2 produces DC voltage used for controlling the buffer BF4, the inverters IN1, IN2 and the solid state relays SSR22, SSR23.

Figure 8:
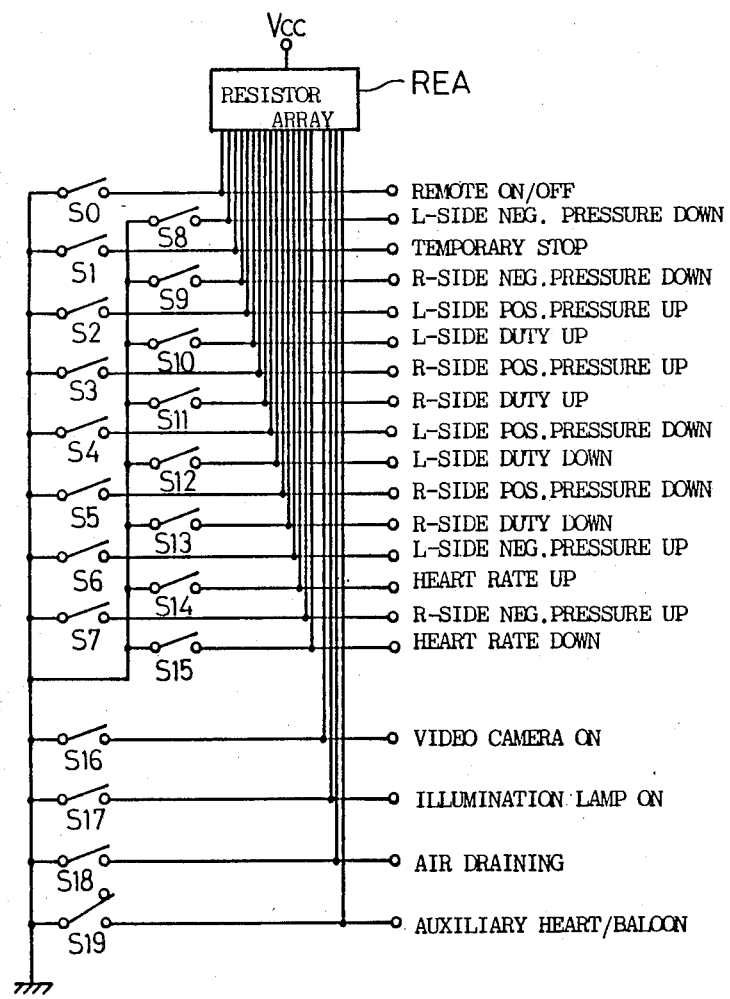
FIG. 8 is an electric circuit diagram showing the construction of a main body side control board shown in FIG. 6.

FIG. 8 illustrates the configuration of the main body side control board MOB in FIG. 6. Description will now be made with reference to FIG. 8. The main body side control board MOB is composed of twenty switches S0 to S19 and a resistor array REA. The switches S0 to S15 have the same functions as the switches B0 to B15 equipped in the remote control board REM, respectively. The switches S0 to S19 function to instruct remote ON/OFF (whether or not the REM is made operable), temporary step (operation of the solenoid valves 52, 53 and 56 is temporarily stopped), L-side positive pressure UP, R-side positive pressure UP, L-side positive pressure DOWN, R-side position pressure DOWN, L-side negative pressure UP, R-side negative pressure UP, L-side negative pressure DOWN, R-side negative pressure DOWN, L-side duty UP, R-side duty UP, L-side duty DOWN, R-side duty DOWN, heart rate UP, heart rate DOWN, video camera ON, illumination lamp ON, air draining and auxiliary heart/balloon pump selection, respectively. A video camera ON signal line and an illumination lamp ON signal line are both connected to the connector in FIG. 7.

Accordingly, upon turning on the switch S16, the solid state relay SSR23 is turned on and AC 100V is applied to the input terminal of the AC/DC converter POW1, thereby to supply a source power (DC12V) to the video camera CAM. Upon turning on the switch S17, the solid state relay SSR22 is turned on so as to supply a source power (AC100V) to the illumination lamp.

In practical use of the monitoring device, the optical fiber cables FB1 and FB2 are integrally mounted to the artificial heart as shown in FIGS. 3a and 3b at the time when the latter is attached to the human body and, thereafter, cloth or bandages are covered over the case 100. When monitoring is needed, upon turning on the switch S16 arranged on the control section 1a of the artificial heart driving apparatus 1, an image picked up by the video camera CAM is displayed on the monitor television unit TV in the display section 1b. The artificial heart can be driven under the optimum conditions by operating the switches on the control section 1a for setting various parameters while observation is kept on the displayed image.

Figure 9A:
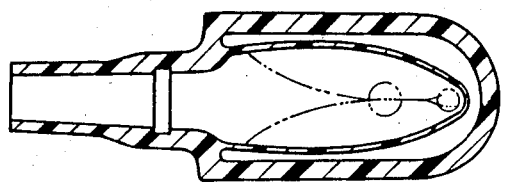
FIGS. 9a and 9b are a transversal and longitudinal sectional view showing positions of optical fibers in a modified embodiment of the present invention, respectively.
Figure 9B:
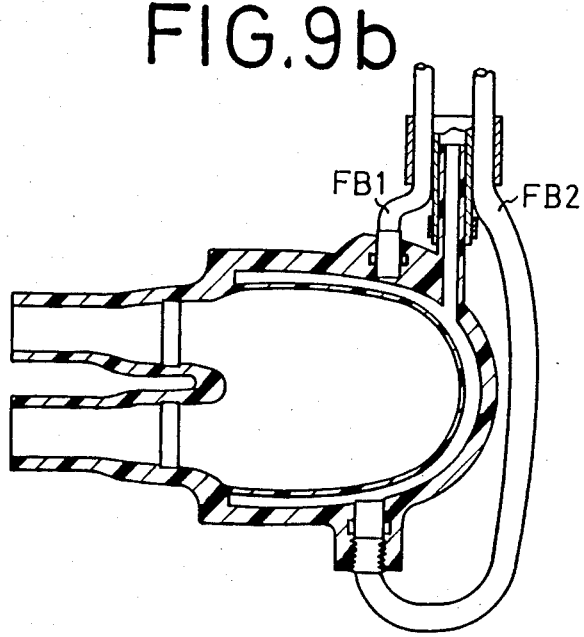
Figure 10A:
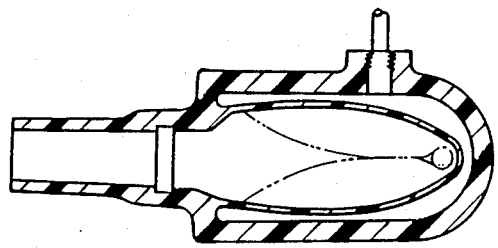
FIGS. 10a and 10b are a transversal and longitudinal sectional view showing positions of optical fibers in another modified embodiment of the present invention, respectively.
Figure 10B:
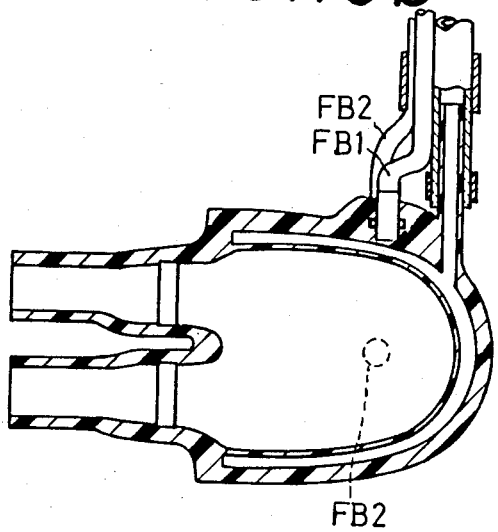

Furthermore, positions where the optical fibers FB1 and FB2 are arranged are not limited to those shown in the foregoing embodiment. As an alternative, the optical fibers may be disposed opposite to each other as shown in FIGS. 9a and 9b, or they may be disposed orthogonally to each other as shown in FIGS. 10a and 10b. In addition, although a single reflection mirror was used in the illustrated embodiment, such mirror may be used in the number of two or more, or may have the curved surface.

According to the present invention, as fully described above, it becomes possible to monitor the actual operating state of an artificial internal organ at all times while it is attached onto the body of a patient.

What we claim is:

1. An apparatus for monitoring an artificial internal organ having a moveable portion comprising:
   an optical fiber having a part thereof fixed to said artificial internal organ such that one fore end of said optical fiber faces the movable portion of said artificial internal organ, for transmitting image information to a remote location;
   photo/electric conversion means coupled to the other end of said optical fiber;
   image display means connected to said photo/electric conversion means; and
   illumination means for emitting a beam of light toward the movable portion of said artificial internal organ.

2. An apparatus for monitoring an artificial internal organ according to claim (1), wherein said illumination means is disposed in a position opposite to the fore end of said optical fiber.

3. An apparatus for monitoring an artificial internal organ according to claim (1), wherein said illumination means is disposed in a position substantially perpendicular to the axis of the fore end of said optical fiber.

4. An apparatus for monitoring an artificial internal organ according to claim (1), wherein said illumination means includes an optical fiber for introducing an illumination light into said artificial internal heart, and a light source for said illumination means is disposed in a location remote from said artificial internal organ.

5. An apparatus for monitoring an artificial internal organ according to claim (1), wherein said artificial internal organ includes at least one light reflecting means disposed on the extended optical axis of said optical fiber.

6. An apparatus for monitoring an artificial internal organ according to claim (1), wherein said photo/electric conversion means is of a video camera and said image display means is of a monitor television unit.

7. An apparatus for monitoring an artificial internal organ according to claim (1), wherein a switch for controlling at least either one of said photo/electric conversion means and said illumination means as well as said image display means are provided in said driving apparatus for artificial internal organ.

* * * * *